(12) United States Patent
Matsunaga et al.

(10) Patent No.: US 9,332,910 B2
(45) Date of Patent: May 10, 2016

(54) ABSENTMINDED STATE DETERMINATION APPARATUS

(71) Applicant: DENSO CORPORATION, Kariya, Aichi-pref. (JP)

(72) Inventors: Shinya Matsunaga, Kariya (JP); Koji Oguri, Handa (JP)

(73) Assignees: DENSO CORPORATION, Kariya (JP); Koji Oguri, Handa (JP)

( * ) Notice: Subject to any disclaimer, the term of this patent is extended or adjusted under 35 U.S.C. 154(b) by 372 days.

(21) Appl. No.: 13/633,982

(22) Filed: Oct. 3, 2012

(65) Prior Publication Data

US 2013/0253841 A1    Sep. 26, 2013

(30) Foreign Application Priority Data

Mar. 21, 2012    (JP) .................................. 2012-63308

(51) Int. Cl.
| | | |
|---|---|---|
| *G08B 23/00* | (2006.01) | |
| *A61B 5/02* | (2006.01) | |
| *A61B 5/18* | (2006.01) | |
| *A61B 5/00* | (2006.01) | |
| *A61B 5/0402* | (2006.01) | |
| *A61B 5/0205* | (2006.01) | |
| *B60W 40/08* | (2012.01) | |

(52) U.S. Cl.
CPC ................ *A61B 5/02* (2013.01); *A61B 5/04021* (2013.01); *A61B 5/18* (2013.01); *A61B 5/6893* (2013.01); *A61B 5/0205* (2013.01); *B60W 2040/0818* (2013.01)

(58) Field of Classification Search
CPC .......... A61B 5/02; A61B 5/18; A61B 5/6893; A61B 5/04021; A61B 5/0205; B60W 2040/0818
See application file for complete search history.

(56) References Cited

U.S. PATENT DOCUMENTS

| | | | | |
|---|---|---|---|---|
| 5,738,104 A | * | 4/1998 | Lo et al. ......................... | 600/521 |
| 7,190,274 B2 | * | 3/2007 | Ihara et al. ..................... | 340/575 |

(Continued)

FOREIGN PATENT DOCUMENTS

| | | |
|---|---|---|
| JP | 2007-229218 A | 9/2007 |
| JP | 2007-290504 A | 11/2007 |

(Continued)

OTHER PUBLICATIONS

Office Action mailed Feb. 19, 2015 issued in corresponding JP patent application No. 2012-063308 (and English translation).

*Primary Examiner* — Thomas Mullen
(74) *Attorney, Agent, or Firm* — Posz Law Group, PLC

(57) ABSTRACT

An absentminded state determination apparatus includes: a data obtaining element for obtaining a time series data of a physiological characteristic value of a participant, wherein a fluctuation component is overlapped on the time series data, and depends on a state of the participant including normal and absentminded states; a detection element for detecting reflecting portions of the time series data, which reflect on the fluctuation component; a counting element for counting the number of the reflecting portions of the time series data in a determination time period between a determination time and a certain past time; and a determination element for determining according to the number of the reflecting portions at the determination time whether the participant is in the absentminded state. The determination time period has a predetermined time width from the certain past time to the determination time.

12 Claims, 9 Drawing Sheets

(56) References Cited

U.S. PATENT DOCUMENTS

| | | | |
|---|---|---|---|
| 7,252,640 B2* | 8/2007 | Ni et al. | 600/538 |
| 8,576,081 B2* | 11/2013 | Hatakeyama et al. | 340/575 |
| 8,655,436 B2* | 2/2014 | Shimizu et al. | 600/519 |
| 8,659,436 B2* | 2/2014 | Ngo | 340/576 |
| 2004/0046666 A1* | 3/2004 | Yasuchi | 340/573.1 |
| 2009/0156948 A1* | 6/2009 | Shimizu et al. | 600/509 |
| 2010/0079294 A1* | 4/2010 | Rai et al. | 340/575 |
| 2010/0168591 A1 | 7/2010 | Tao et al. | |
| 2010/0234747 A1* | 9/2010 | Hatakeyama | 600/509 |
| 2011/0193707 A1* | 8/2011 | Ngo | 340/576 |
| 2011/0313259 A1* | 12/2011 | Hatakeyama et al. | 600/300 |

FOREIGN PATENT DOCUMENTS

| | | |
|---|---|---|
| JP | 2008-035964 A | 2/2008 |
| JP | 2009-172292 A | 8/2009 |

\* cited by examiner

FIG. 3   BREATHING RATE REDUCTION
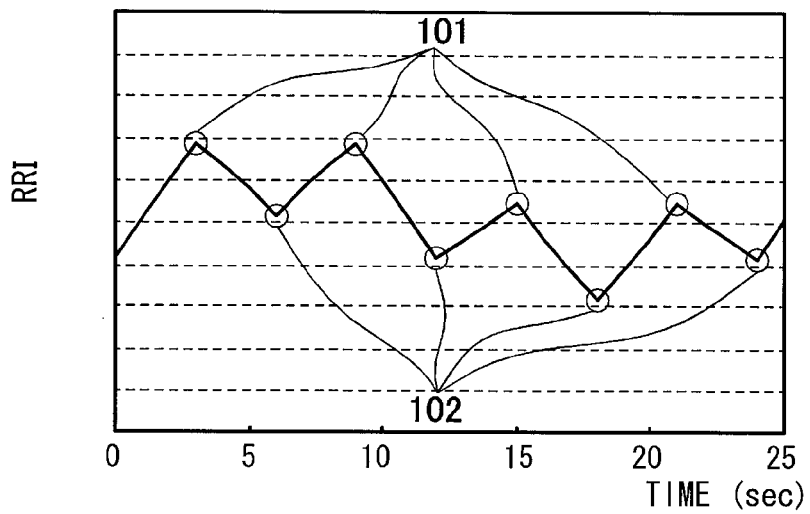
FIG. 4   PARASYMPATHETIC SUP HRV
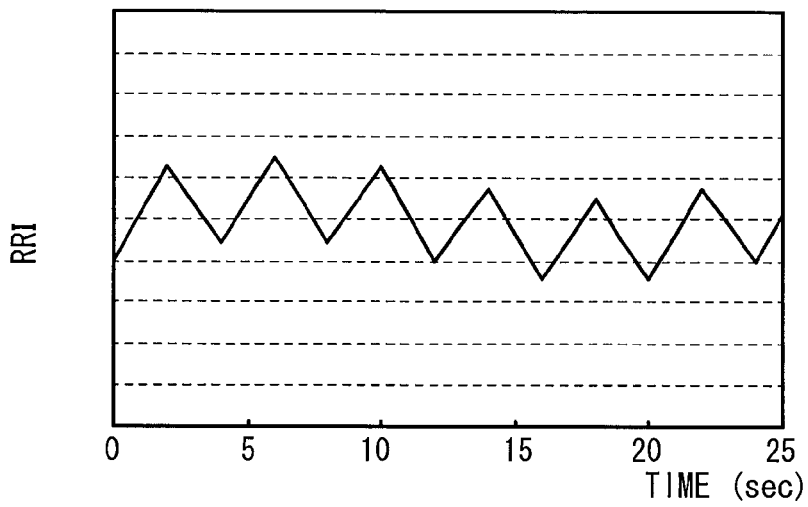
FIG. 5   BREATHING RATE INCREASE
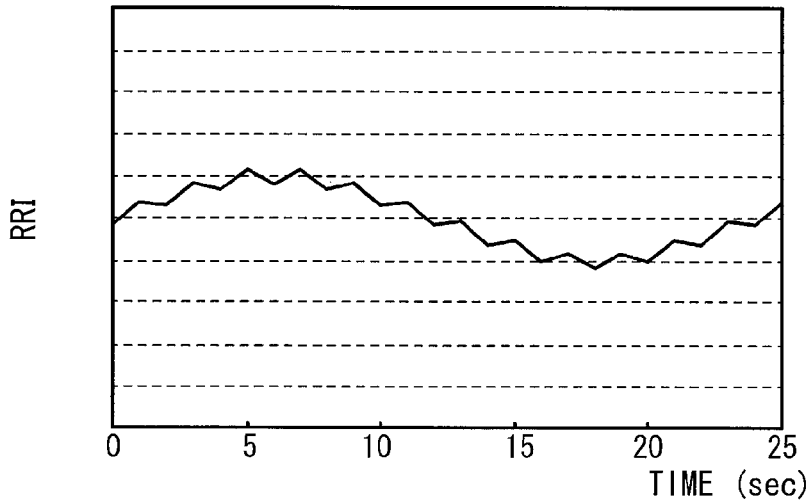

ABSENTMINDED STATE DETERMINATION APPARATUS

CROSS REFERENCE TO RELATED APPLICATION

This application is based on Japanese Patent Application No. 2012-63308 filed on Mar. 21, 2012, the disclosure of which is incorporated herein by reference.

TECHNICAL FIELD

The present disclosure relates to an absentminded state determination device for determining whether a state of a user is an absentminded state.

BACKGROUND

Conventionally, JP-A-2008-35964 teaches a method for determining sleepiness of a driver of a vehicle. In the method, frequency analysis such as Fourier transformation is executed to time series data of a period of heart rate, so that heart rate variability (HRV) rate is retrieved. Based on the heart rate variability, the sleepiness of the driver is determined.

When the state of the driver of the vehicle is determined, it is preferable to determine not only a sleepiness state (or asleep state) of the driver but also an absentminded state, in which the driver is in a daze before the driver gets sleepy. However, in the prior art, there is no suggestion about determination of the absentminded state.

Further, the frequency analysis with using the Fourier transformation is much affected by a noise such as a body motion of the user and a vibration of the vehicle. Specifically, when data with the noise is Fourier transformed, spectrum power data obtained by the Fourier transformation is largely varied with a magnitude of the noise. Thus, the accuracy of the spectrum power data is low. In the above method, the sleepiness is determined with utilizing the frequency analysis, which is susceptibility to noise. In some cases, the accuracy of determination of the state of the user is low.

SUMMARY

It is an object of the present disclosure to provide an absentminded state determination device for determining both of the asleep state and the absentminded state. Further, the absentminded state determination device is resistant to noise.

According to an aspect of the present disclosure, an absentminded state determination apparatus includes: a data obtaining element for obtaining a time series data of a physiological characteristic value of a participant, wherein a fluctuation component is overlapped on the time series data, and the fluctuation component depends on a state of the participant including a normal state and an absentminded state so that the fluctuation component is changeable; a detection element for detecting a plurality of reflecting portions of the time series data, wherein the plurality of reflecting portions reflect on the fluctuation component; a counting element for counting the number of the reflecting portions of the time series data in a determination time period, which is disposed between a determination time and a certain past time; and a determination element for determining according to the number of the reflecting portions at the determination time whether the participant is in the absentminded state. The determination time period has a predetermined time width from the certain past time to the determination time.

In the above apparatus, by measuring the number of the reflecting portions, the apparatus can determine whether the participant is in the absentminded state. Even if a noise is overlapped on the time series data, the number of the reflecting portions is not easily affected by the magnitude of the noise. Thus, the apparatus can determine the absentminded state without depending on the noise, compared with the conventional method with using a frequency analysis method.

BRIEF DESCRIPTION OF THE DRAWINGS

The above and other objects, features and advantages of the present disclosure will become more apparent from the following detailed description made with reference to the accompanying drawings. In the drawings:

FIG. 3 is a graph showing time series data of a period of heart rate when a breathing rate is reduced;

FIG. 4 is a graph showing time series data of a period of heart rate when a parasympathetic is superior to a sympathetic;

FIG. 5 is a graph showing time series data of a period of heart rate when a breathing rate increases;

DETAILED DESCRIPTION

Figure 1:
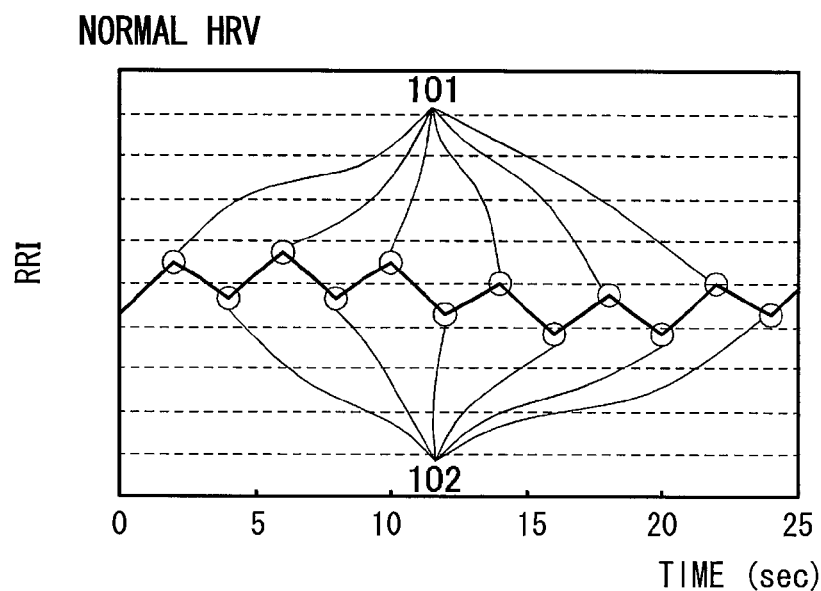
FIG. 1 is a graph showing time series data of a period of heart rate in a normal state.
Figure 2:
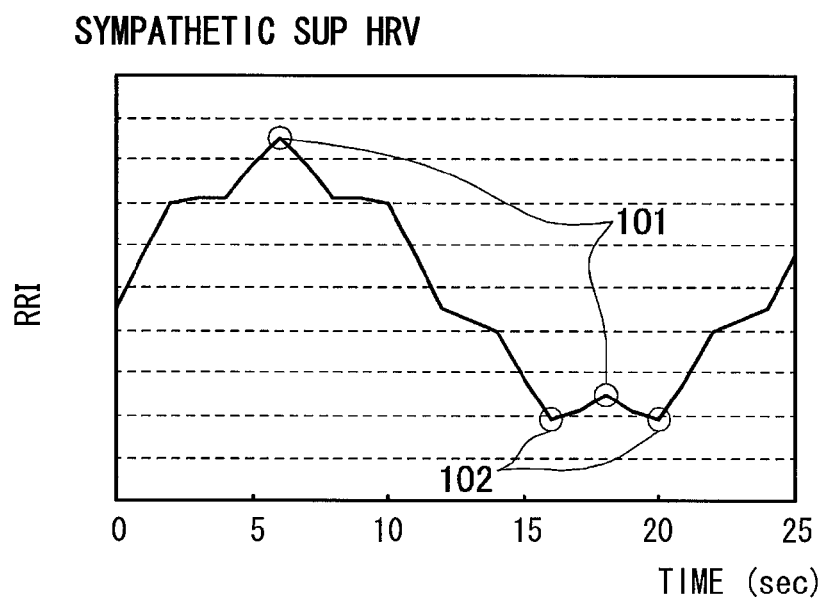
FIG. 2 is a graph showing time series data of a period of heart rate when a sympathetic is superior to a parasympathetic.

An absentminded state determination apparatus according to an example embodiment will be explained with reference to the drawings. In the present embodiment, an absentminded state of a driver of a vehicle is a determination object. The absentminded state of the driver is determined based on knowledge such that a fluctuation component of time series data of a period of heart rate is different between a normal state and the absentminded state of the driver. Thus, the knowledge will be explained initially. FIGS. 1 to 5 show time series data of a period of heart rate in various states of a human body. Specifically, FIG. 1 shows time series data of a period of heart rate in a normal state. FIG. 2 shows time series data of a period of heart rate when a sympathetic is superior to a parasympathetic. FIG. 3 shows time series data of a period of heart rate when a breathing rate is reduced. FIG. 4 shows time series data of a period of heart rate when a parasympathetic is superior to a sympathetic. FIG. 5 shows time series data of a period of heart rate when a breathing rate increases. In FIGS. 1 to 5, the period of heart rate is provided by a distance RRI in a R wave of an electrocardiogram signal. In FIGS. 1 to 5, the vertical axis and the horizontal axis are the same.

As shown in FIGS. 1 to 5, even when the state of the human body is any one of states, an increase and a decrease of the distance RRI are alternately repeated. This phenomenon is defined as a fluctuation. The characteristics of the fluctuation depend on the state of the human body. Specifically, the distance RRI is fluctuated largely and slowly with time when the sympathetic is superior to the parasympathetic so that the human body is active, as shown in FIG. 2, compared with data in FIG. 1. Thus, in this case, the distance RRI has a long period. Specifically, when the sympathetic is superior to the parasympathetic, a low frequency fluctuation is overlapped on the time series data of the distance RRI. The low frequency fluctuation provides a low frequency fluctuation component. Further, a fluctuation range of the low frequency fluctuation component is large. Further, as show in FIG. 3, when the breathing rate is reduced, the distance RRI is slowly fluctuation with time, compared with data in FIG. 1. Specifically, when the breathing rate is reduced from the normal state, the low frequency fluctuation component is overlapped on the time series data of the distance RRI. Here, the low frequency fluctuation component has a frequency in a range between 0.04 Hz and 0.15 Hz.

On the other hand, when the parasympathetic is superior to the sympathetic so that the human body gets rest, as shown in FIG. 4, and when the breathing rate increases, as shown in FIG. 5, the distance RRI fluctuates with a short period, compared with the data in FIG. 1. Specifically, a high frequency fluctuation is overlapped on the time series data of the distance RRI in FIGS. 4 and 5. The high frequency fluctuation provides a high frequency fluctuation component. Here, the frequency of the high frequency fluctuation component is in a range between 0.15 Hz and 0.4 Hz.

The present inventor executes an experiment such that a research participant actually drives the vehicle, and the time series data of the distance RRI of the driver is measured, and further, the driver subjectively evaluate a state of the driver. As an experimental result, when the state of the driver is the absentminded state, the time series data is similar to the data in FIGS. 2 and 3. Specifically, when the driver is in the absentminded state, i.e., when the driver is in a daze, the low frequency fluctuation component is overlapped on the time series data of the distance RRI. When the driver is in the absentminded state, a risk of an accident increases. Thus, in order to avoid the risk, the sympathetic functions instinctively so as to switch the body to the normal state. Regarding the breathing rate, when the driver is in the absentminded state, the breathing rate of the driver is reduced, similar to the sleeping time.

Further, a research participant simulates the driving of the vehicle with using a drive simulator under a condition similar to the above experiment. On the contrary of the above experiment of the driving, even when the participant is in the absentminded state, the high frequency fluctuation component is overlapped on the time series data, as shown in FIG. 4. This is because there is no actual dangerous situation of an accident even if the driver simulates the driving and the driver goes into the absentminded state, compared with an actual driving situation. Thus, the sympathetic nerve system does not work actively, compared with the actual driving situation. Thus, a phenomenon such that the low frequency fluctuation component is overlapped on the time series data of the distance RRI when the participant goes into the absentminded state is remarkably exposed in a case where the driver as the participant actually drives the vehicle.

In the present embodiment, it is determine whether the low frequency fluctuation component in FIGS. 2 and 3 is overlapped on the time series data of the distance RRI, so that it is detected whether the driver goes into the absentminded state. In the present embodiment, a method for detecting the low frequency fluctuation component is characteristic. Specifically, the low frequency fluctuation component is detected according to the number of peaks of the time series data of the distance RRI and the number of troughs of the time series data of the distance RRI. Both of the peaks and the troughs are defined as TP. Here, the peak represents a data point of the time series data of the distance RRI, which has the distance RRI larger than each adjacent data point. In FIGS. 1 to 3, the peak is shown as 101. The trough represents a data point of the time series data of the distance RRI, which has the distance RRI smaller than each adjacent data point. In FIGS. 1 to 3, the trough is shown as 102. As shown in FIGS. 1 to 3, when comparing in a certain time period having the same time width, the number of the peaks 101 and troughs 102 in a case where the driver is in the absentminded state, i.e., where the low frequency fluctuation is generated is smaller than the number of the peaks 101 and troughs 102 in a case where the driver is in the normal state. Here, the number of the peaks 101 and the troughs 102 is the number of TPs. In the present embodiment, when the number of TPs is smaller than in the normal state, it is determined that the driver is in the absentminded state. The detailed embodiment will be explained as follows.

Figure 6:
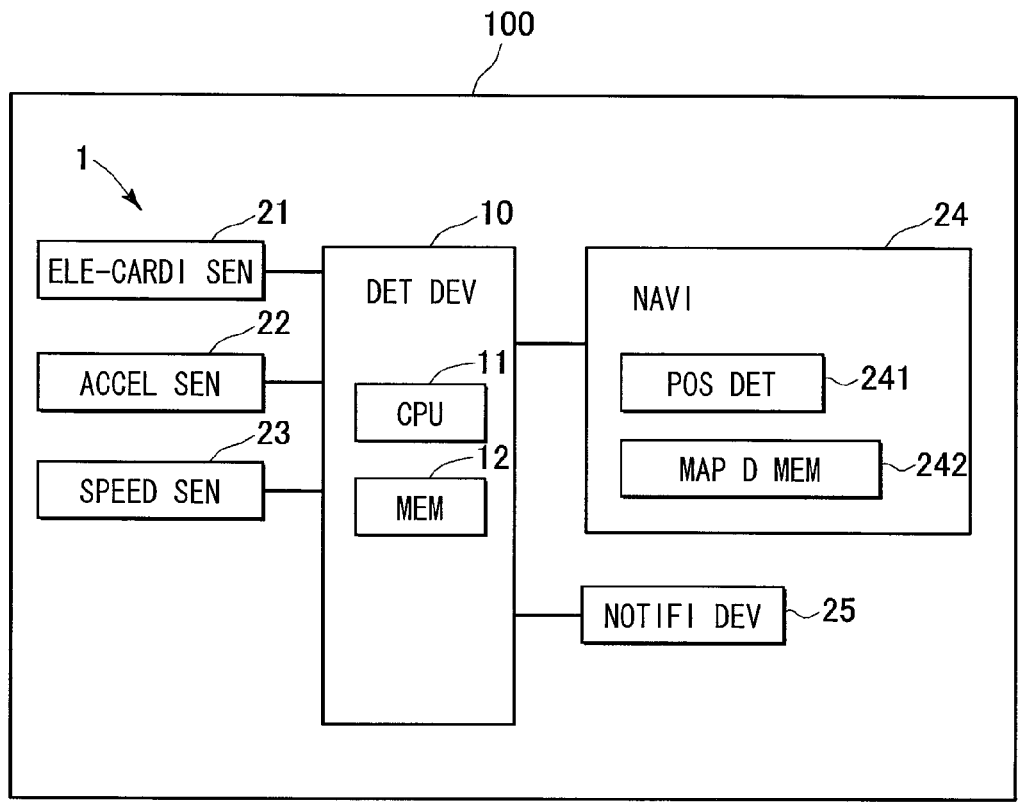
FIG. 6 is a diagram showing an absentminded state determination system.
Figure 7:
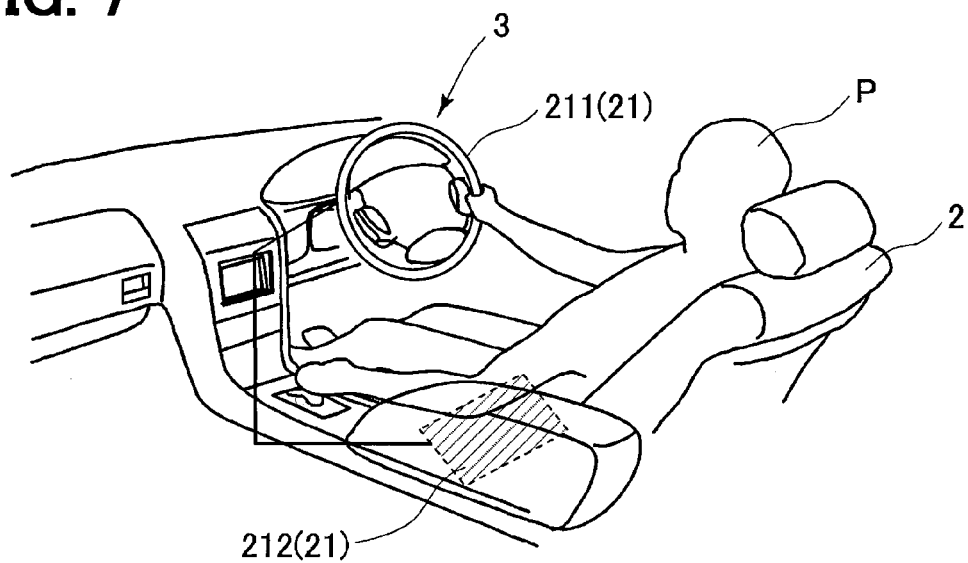
FIG. 7 is a diagram showing a setting position of an electrocardiogram sensor.
Figure 9:
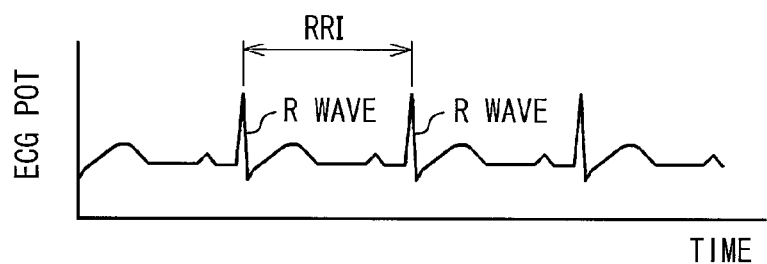
FIG. 9 is a diagram showing an electrocardiogram signal.

FIG. 6 shows an absentminded state determination system 1 mounted on a vehicle 100. The system 1 includes a determination device 10 as an absentminded state determination device, an electrocardiogram sensor 21, an acceleration sensor 22, a vehicle speed sensor 23, a navigation device 24 and a notification device 25. The electrocardiogram sensor 21 measures an electrocardiogram signal of the driver P, as shown in FIG. 9. As shown in FIG. 7, the electrocardiogram sensor 21 includes a pair of electrodes 211, 212, which is arranged at a portion contacting a body of the driver P. In FIG. 7, one electrode 211 is arranged on a steering wheel 3, which contacts a palm of the driver P. The other electrode 212 is arranged on a cushion of a driver seat 2, which contacts a hip of the driver P. Specifically, the other electrode 212 is arranged on a backside of a cushion cover. Thus, even if both palms of the driver P do not contact the steering wheel 3, the electrocardiogram signal of the driver P is detected, i.e., when one of the palms of the driver P contact the steering wheel 3, the electrocardiogram signal of the driver P is detected. Here, alternatively, one electrode 211 of the electrocardiogram sensor 21 may be arranged on a right side of the steering wheel 3, and the other electrode 212 may be arranged on a left side of the steering wheel 3. In this case, when both palms of the driver P contact the steering wheel 3, the electrocardiogram signal of the driver. P is detected. The electrocardiogram signal detected by the electrocardiogram sensor 21 is input into the determination device 10.

The acceleration sensor 22 measures acceleration of the vehicle 100. The vehicle speed sensor 23 measures a vehicle speed of the vehicle 100. The navigation device 24 includes a position detector 241 for detecting a current position of the vehicle 100 and a map data memory 242 for storing road map data. The position detector 241 includes a GPS receiver for receiving a GPS signal, a vehicle speed sensor, a gyro sensor and the like. The navigation device 24 searches a route from the current position to a destination according to the road map data stored in the memory 24. Further, the navigation device 24 guides the driver to drive the vehicle along the searched route. The road map data includes information about a type of a road such as an express way, a highway, a normal road and a street. The information about the type of the road is defined as road type information. The navigation device 24 specifies the type of the road, on which the vehicle is driving currently, according to the current position detected by the position detector 241 and the road type information.

The notification device 25 notifies the driver of the absentminded state when the driver is in the absentminded state. Specifically, the notification device 25 is a speaker for notifying a sound. Alternatively, the notification device 25 is a display for displaying the notification information.

Figure 8:
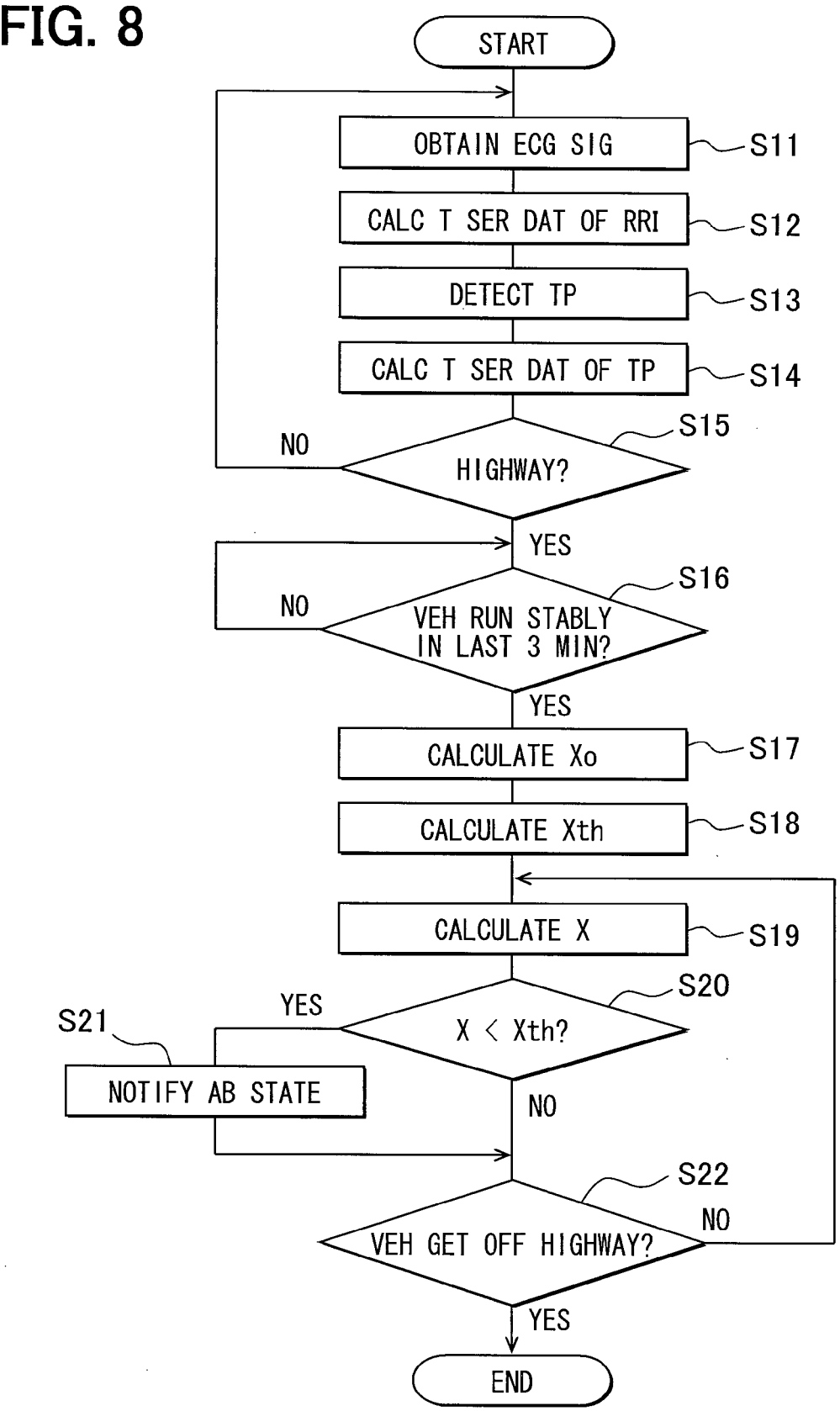
FIG. 8 is a flowchart showing a process in CPU.

The determination device 10 determines whether the driver is in the absentminded state. The determination device 10 includes a CPU 11 for executing various processes, a memory such as a ROM and a RAM for storing various information, and the like. The CPU 11 executes a process for determining whether the driver is in the absentminded state, according to a program stored in the memory 12. The process to be executed by the CPU 11 will be explained. Here, FIG. 8 shows a flowchart of the process executed by the CPU 11. The CPU 11 starts to execute the process in FIG. 8 when the engine of the vehicle 100 starts, and the CPU 11 is energized. The CPU 11 repeats to execute the process in FIG. 8 until the engine stops running.

Figure 10:
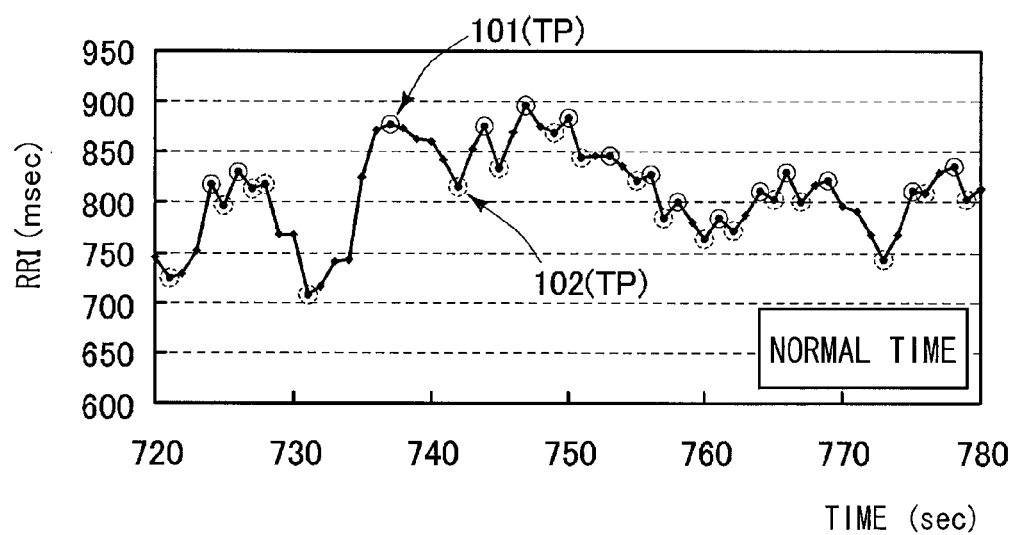
FIG. 10 is a graph showing time series data when the driver is in a normal state.
Figure 11:
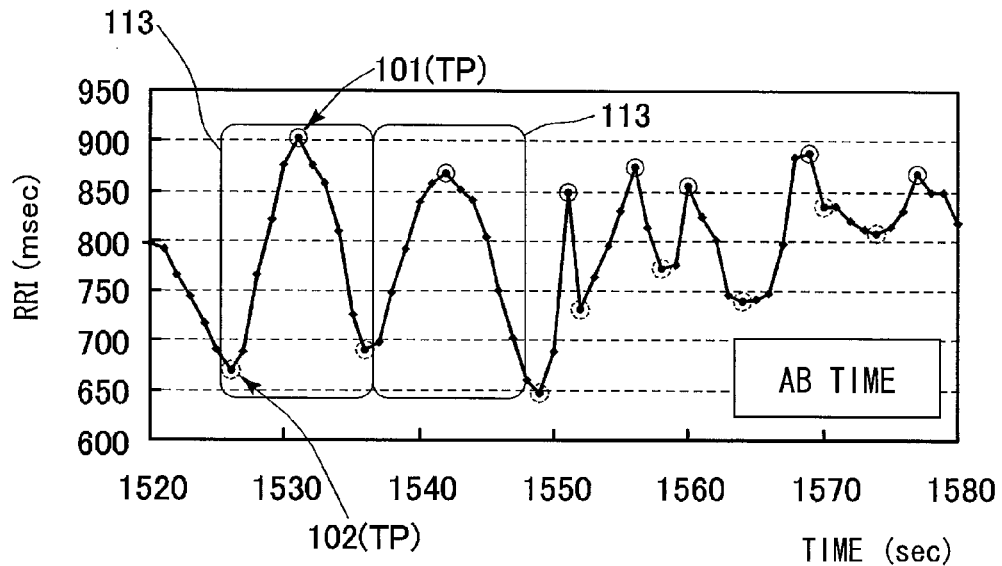
FIG. 11 is a graph showing time series data when the driver is in an absentminded state.

In step S11, the CPU 11 obtains the electrocardiogram signal (ECG signal) of the driver P, which is detected by the electrocardiogram sensor 21. FIG. 9 shows the electrocardiogram signal obtained in step S11. In FIG. 9, a horizontal axis represents time, and a vertical axis represents an electrocardiogram potential. Next, in step S12, the CPU 11 calculates the distance RRI at each time in predetermined intervals from the electrocardiogram signal. Here, in the present embodiment, the predetermined interval is one second. The distance RRI is a distance between adjacent R waves. Thus, the CPU 11 obtains the time series data of the distance RRI. FIGS. 10 and 11 show the time series data of the distance RRI obtained in step S12. FIG. 10 shows the time series data when the driver is in the normal state. FIG. 11 shows the time series data when the driver is in the absentminded state. An interval between adjacent data points for providing the time series data in FIGS. 10 and 11 is one second. The time series data obtained in step S12 is stored in the memory 12.

Then, in step S13, the CPU 11 detects the peaks and the troughs TP among the data points for providing the time series data. Specifically, three series data points a, b, c are selected in the time series data. When the middle data point b has the distance RRI, which is larger than the data points a, c, the CPU 11 determines that the data point b is the peak. When the middle data point b has the distance RRI, which is smaller than the data points a, c, the CPU 11 determines that the data point b is the trough. In FIGS. 10 and 11, the peaks 101 detected in step S13 are shown as a data point surrounded with a solid circle. The troughs 102 detected in step S13 are shown as a data point surrounded with a dotted circle.

Figure 12:
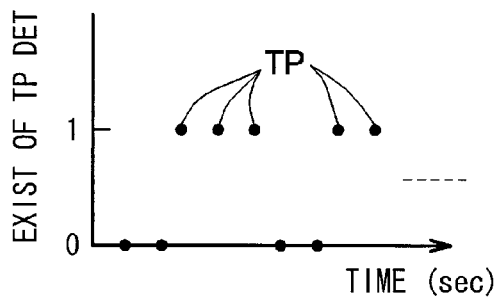
FIG. 12 is a diagram showing time series data of TP.

In step S14, the CPU 11 calculates the time series data of the peaks and the troughs TP, which are detected in step S13. Specifically, the CPU 11 calculates the time series data, which represents that the data point in the time series data of the distance RRI at certain time is the peak or the trough TP. FIG. 12 shows the time series data of the peaks and the troughs TP calculated in step S14. In FIG. 12, a horizontal axis represents time, which is the same as the time series data of the distance RRI. A zero point in the vertical axis represents that the data point of the distance RRI is not the peak and the trough TP. A point "1" in the vertical axis represents that the data point of the distance RRI is the peak or the trough TP. Here, the calculated time series data of the peak and trough TP is stored in the memory 12.

Next, in step S15, the CPU 11 communicates with the navigation device 24, so that the CPU 11 determines whether the vehicle runs or enters into the highway (or the express way). This is because, in the present embodiment, the determination whether the driver is in the absentminded state is limited to time when the vehicle runs on the highway. Here, when the driver accelerates and decelerates the vehicle frequently, the sympathetic nerve system mainly functions, so that the low frequency fluctuation component may be overlapped on the time series data of the distance RRI even in a case where the driver is in the normal state. When the vehicle runs on the highway, the CPU 11 can determine whether the driver is in the absentminded state since there is not traffic light on the highway so that the driver does not accelerate and decelerate the vehicle frequently. Thus, in the present embodiment, the determination of the absentminded state of the driver is limited in a case where the vehicle runs on the highway.

In step S15, when the vehicle does not enter into the highway, i.e., when the determination of step S15 is "NO," it returns to step S11. In this case, even when the vehicle does not enter into the highway, the CPU 11 continues to execute steps S11 to S14. When the vehicle enters into the highway, i.e., when the determination of step S15 is "YES," it proceeds to step S16. Even when the CPU 11 executes steps after step S16, the CPU 11 continues to execute steps S11 to S14, so that the CPU 11 obtains the time series data of the distance RRI and the time series data of the peak and trough TP while running on the highway.

In step S16, after the vehicle enters into the highway, the CPU 11 determines whether the vehicle runs stably in last three minutes at the present time as standard time. Specifically, the CPU 11 determines whether the acceleration of the vehicle within last three minutes detected by the acceleration sensor 22 is equal to or smaller than a predetermined value. Here, the predetermined value is set to be a comparatively small value, which is defined such that, when the acceleration is the predetermined value, the vehicle 100 is deemed to run at a constant speed. Thus, in step S16, the CPU 11 determines whether the vehicle runs at almost the constant speed in last three minutes without rapidly accelerating and decelerating frequently. In step S16, in addition to the acceleration of the vehicle, the CPU 11 may determine according to the speed of the vehicle detected by the vehicle speed sensor 23 whether the vehicle runs at the constant speed. Alternatively, the CPU 11 may determine according to only the speed of the vehicle detected by the vehicle speed sensor 23 whether the vehicle runs at the constant speed. In this case, for example, when the speed of the vehicle in last three minutes is in a predetermined speed range, the CPU 11 determines whether the vehicle runs at the constant speed. Here, the predetermined speed range is, for example, in a range between 80 km/h and 100 km/h. The CPU 11 executes step S16 since the CPU 11 determines a certain time period as a standard time period, in which the CPU 11 estimates that the driver is in the normal state with small or no fluctuation of the distance RRI caused by the acceleration and the deceleration. Specifically, for example, a certain time period, in which the vehicle has comparatively large acceleration just after the vehicle enters into a main lane of the highway from an interchange or a ramp way, is eliminated from the standard time period. It is assumed that the driver is in the normal state initially just after the vehicle enters into the highway. Thus, in step S16, the CPU 11 determines whether the vehicle runs stably within last three minutes until predetermined time has elapsed after the vehicle enters into the highway. Here, the predetermined time is, for example, ten minutes.

The CPU 11 continues to execute step S16 until the vehicle runs stably in last three minutes. When the vehicle runs stably, i.e., when the determination in step S16 is "YES," it goes to step S17. In step S17, the CPU 11 determines that the last three minutes are defined as the standard time period, in which the CPU 11 determines that the vehicle runs stably. Here, the time series data of the distance RRI in the standard time period is deemed to be the same as the time series data in the normal state in FIG. 10. Further, in step S17, the CPU 11 calculates the number Xo of peaks and troughs TP in the standard time period according to the time series data of peaks and troughs TP within the standard time period calculated in step S14. Specifically, in FIG. 12, the CPU 11 counts the number of data points "1" in the standard time period of three minutes. Here, the number Xo calculated in step S17 is deemed to be the number of peaks and troughs TP in a case where the driver is in the normal state.

Next, in step S18, based on the number Xo calculated in step S17, the CPU 11 sets the threshold value Xth of the peaks and troughs, which distinguishes the normal state and the absentminded state of the driver P. Here, the threshold value Xth is defined as a first threshold value Xth. Specifically, the number of peaks and troughs in the normal state may be fluctuated to some extent. Thus, in order to prevent from determining frequently that the driver is in the absentminded state, the CPU 11 sets the threshold value Xth to be smaller than the number Xo of the peaks and troughs. For example, the CPU 11 sets the threshold value Xth by multiplying the number Xo and a predetermined ratio such as 80%.

Under a condition that the CPU 11 sets the threshold value Xth in step S18, the CPU 11 starts to determine whether the driver is in the absentminded state. Specifically, when the driver drives the vehicle after the CPU 11 executes step S18, in step S19, the CPU 11 calculates the number X of peaks and troughs TP in a determination time period according to the time series data of peaks and troughs TP at the present time as standard time in the determination time period of last three minutes calculated in step S14. Here, the number X of peaks and troughs TP in the determination time period is defined as a first number X. Then, in step S20, the CPU 11 determines whether the first number X is smaller than the threshold value Xth. When the first number X is smaller than the threshold value Xth, i.e., when the determination of step S20 is "YES," it is considered that the number X of peaks and troughs TP is reduced since the low frequency fluctuation component having a large magnitude is overlapped on the time series data of the distance RRI, as shown in FIG. 11. In this case, based on the previously described knowledge, the CPU 11 determines that the driver is in the absentminded state at the present time in step S21. Further, in step S21, the CPU 11 notifies the driver via the notification device 25 that the driver is in the absentminded state. Thus, the system 1 notifies the driver that the driver is in the absentminded state before the driver gets sleepy. As a result, the system 1 promotes the driver to get rest. After step S21, it goes to step S22.

In step S20, when the number X is larger than the threshold value Xth, i.e., when the determination of step S20 is "NO," the CPU 11 determines that the driver is not in the absentminded state, i.e., the driver is in the normal state. Thus, it goes to step S22 without executing step S21.

In step S22, the CPU 11 communicates with the navigation device 24, so that the CPU 11 determines whether the vehicle 100 gets off the highway. When the CPU 11 determines that the vehicle 100 does not get off the highway, i.e., when the determination of step S22 is "NO," it returns to step S19. Specifically, when the vehicle runs on the highway, the CPU 11 repeats steps S19 to S22. Thus, the CPU 11 determines at each time whether the driver is in the absentminded state. When the vehicle gets off the highway, i.e., when the determination in step S22 is "YES," the CPU 11 ends to execute the process in FIG. 8. Here, in this case, the CPU 11 starts to execute the process in FIG. 8 again so that it goes to step S11. When the vehicle 100 is running, the CPU 11 obtains the time series data of the distance RRI in step S12, detects the peaks and troughs TP in step S13, and calculates the time series data of peaks and troughs TP in step S14.

Explanation of the method for determining whether the driver is in the absentminded state according to the number of peaks and troughs TP is completed.

Figure 13:
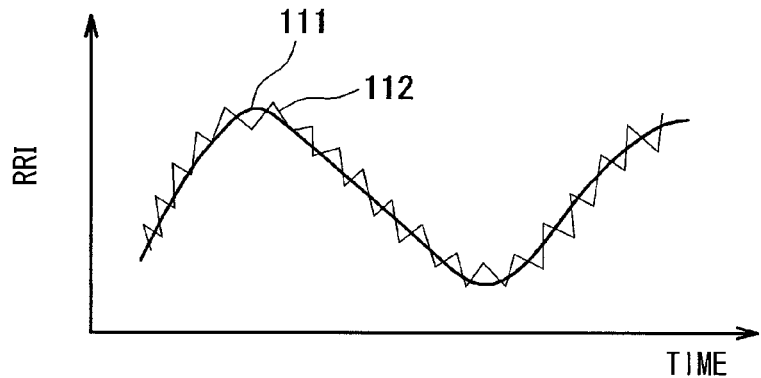
FIG. 13 is a graph showing time series data of RRI with a low frequency fluctuation and a high frequency fluctuation.

Here, based on the above experiments, the present inventors obtains knowledge that tendency of the high frequency fluctuation component overlapping on the time series data of the distance RRI in FIG. 4 in a case where the parasympathetic nerve system functions mainly appears exceptionally in the time series data of the distance RRI when the driver is in the absentminded state, in addition to the tendency in FIG. 2 of the low frequency fluctuation component overlapping on the time series data. Here, FIG. 13 shows the time series data of the distance RRI in case of the above exceptional case. As shown in FIG. 13, when the driver is in the absentminded state, the low frequency fluctuation component curve 111 and the high frequency fluctuation component curve 112 are overlapped on the time series data exceptionally. In this case, since the peaks and troughs TP caused by the high frequency fluctuation component curve 112 affects the number of peaks and troughs TP, the number of peaks and troughs TP may be almost equal to the normal state although the driver is in the absentminded state. In order to remove the influence of the high frequency fluctuation component curve 112, it is considered that a filtering process is executed so that the high frequency fluctuation component is eliminated from the time series data. Based on the time series data of peaks and troughs TP after the high frequency fluctuation component is eliminated, the CPU 11 may determine whether the driver is in the absentminded state. However, in this case, the high frequency fluctuation component is eliminated from the time series data in the standard time period (i.e., the time series data in case of the normal state). Thus, a difference of the time series data between the standard time period and the absentminded state is made small. Thus, in the present embodiment, in order to surely determine the absentminded state even in the above exceptional case, the CPU 11 determines according t a second method whether the driver is in the absentminded state. The second method is different from the above method for determining the absentminded state according to the number of peaks and troughs TP.

Figure 14:
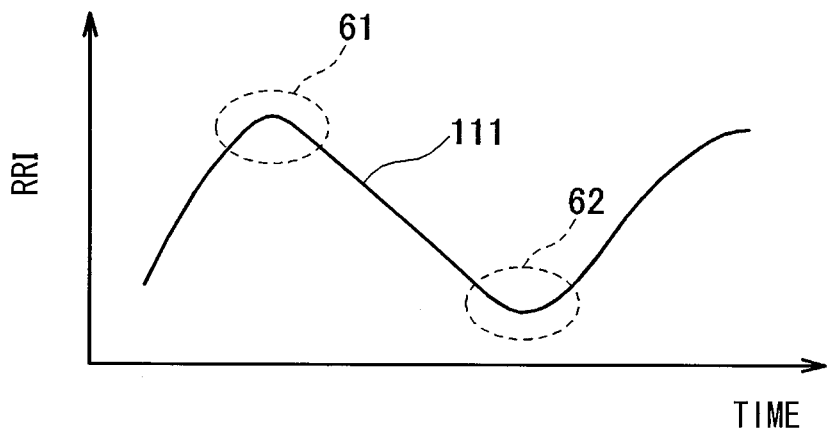
FIG. 14 is a graph showing time series data, which is prepared by deleting a curve from the time series data of RRI in FIG. 13.

The second method for determination will be explained as follows. As shown in FIG. 11, when the driver is in the absentminded state, the low frequency fluctuation having a large magnitude is frequently generated. The low frequency fluctuation having the large magnitude is shown as 113, and is defined as a low frequency large fluctuation. Thus, in the second method, the low frequency large fluctuation is detected. The absentminded state of the driver is determines based on the number of occurrence of the low frequency large fluctuation in a predetermined time period as a detection time period. Specifically, as shown in FIG. 13, assuming that the high frequency fluctuation component is overlapped on the time series data even when the driver is in the absentminded state, in the second method, the high frequency fluctuation component is removed from the time series data of the distance RRI. Thus, the high frequency fluctuation component curve 112 is removed. FIG. 14 shows the time series data (corresponding to a curve 111) after the high frequency fluctuation component curve 112 is removed from the time series data in FIG. 13.

Figure 15:
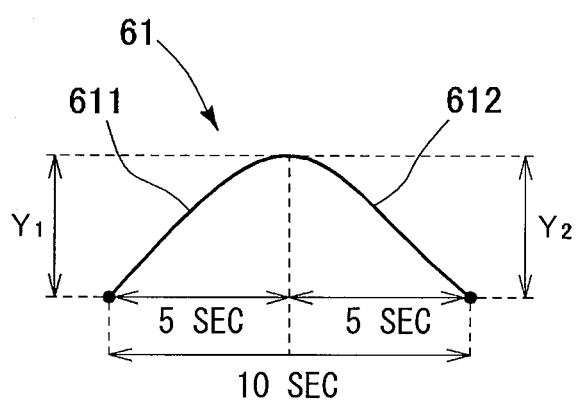
FIG. 15 is a graph showing a partially enlarged view of an upper convexity.
Figure 16:
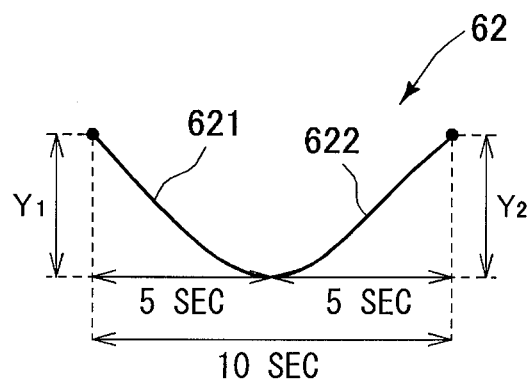
FIG. 16 is a graph showing a partially enlarged view of a lower convexity.

Then, in the curve 111 in FIG. 14, an upper convexity 61 and a dower convexity 62 are detected. The upper convexity 61 protrudes toward a direction, to which the distance RRI becomes large. The lower convexity 62 protrudes toward a direction, to which the distance RRI becomes small. Here, FIG. 15 shows an enlarged view of the upper convexity 61, and FIG. 16 shows an enlarged view of the lower convexity 62. As shown in FIGS. 15 and 16, the upper convexity 61 and the lower convexity 62 have the protrusion shape in a predetermined time interval. In this embodiment, the predetermined time interval is 10 seconds, and corresponds to a first time width. Thus, the upper convexity 61 and the lower convexity 62 are deemed to reflect on the fluctuation having a long cycle, i.e., the low frequency fluctuation. Here, the first time width such as ten seconds of the upper convexity 61 and the lower convexity 62 is longer than the cycle of the high frequency fluctuation. Here, the high frequency fluctuation has a frequency in a range between 0.15 Hz and 0.4 Hz, so that the cycle of the high frequency fluctuation is in a range between 2.5 seconds and 6.7 seconds. The variations Y1, Y2 of the distance RRI in the upper convexity 61 or the lower convexity 62 are larger than the variation of the distance RRI in the standard time period (i.e., in the normal state). Thus, the upper convexity 61 and the lower convexity 62 are deemed to reflect on the large fluctuation, which provides large variation of the distance RRI. Since the upper convexity 61 and the lower convexity 62 are deemed to reflect on the large fluctuation (i.e., the low frequency large fluctuation), in the second method, the absentminded state is determined according to the number of upper convexities 61 and the lower convexities 62. The second method for determining the absentminded state including a detection step for detecting the upper convexities 61 and the lower convexities 62 will be explained as follows.

Figure 17:
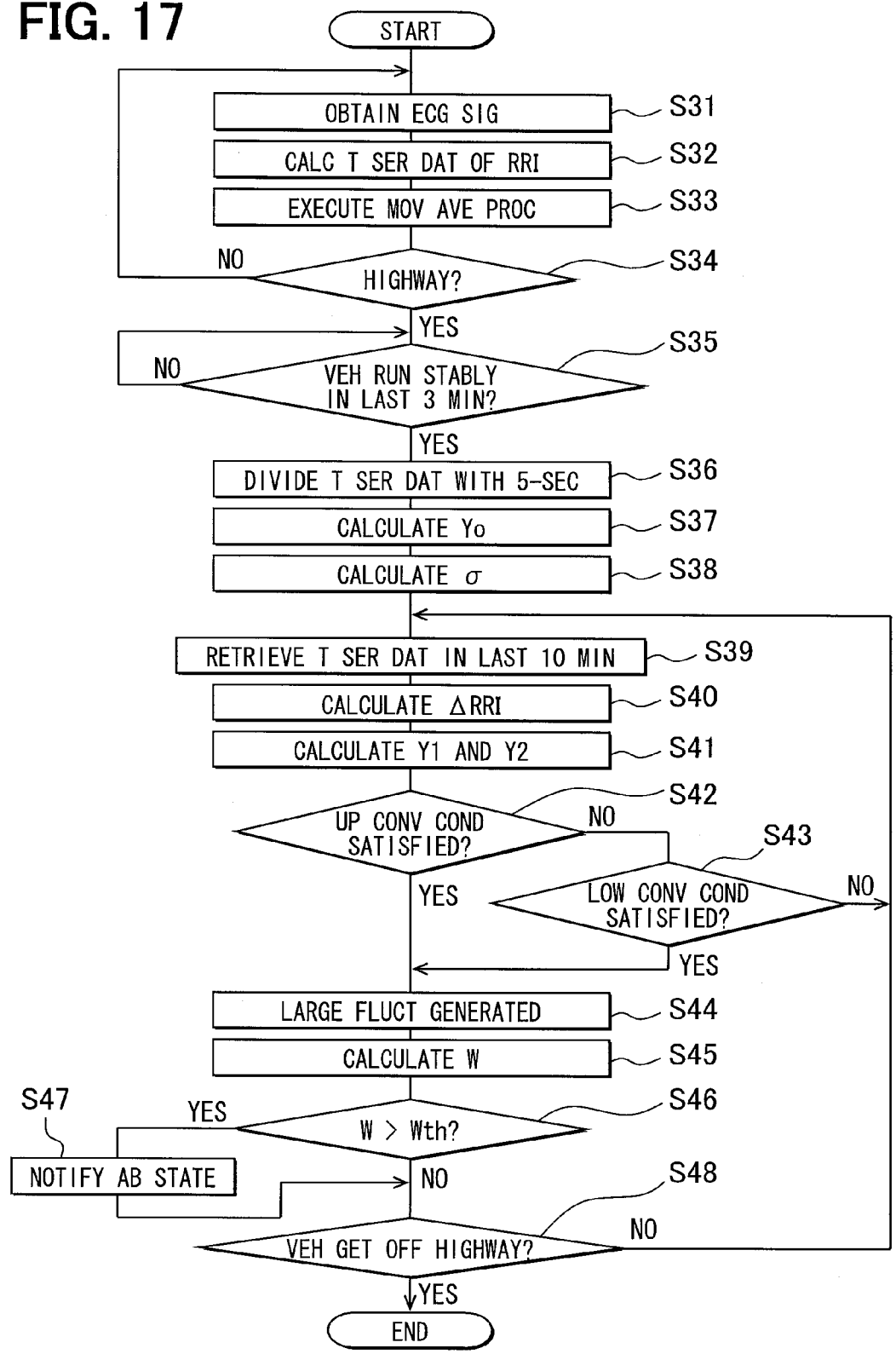
FIG. 17 is a flowchart showing another process in CPU, to which a second method for determining the absentminded state is reflected.

FIG. 17 shows a flowchart of the process to be executed by the determination device 10 (i.e., the CPU 11), which provides the second method. In the process in FIG. 17 may be executed in parallel to the process in FIG. 8. Step S31 in FIG. 17 corresponds to step S11 in FIG. 8. Step S32 in FIG. 17 corresponds to step S12 in FIG. 8. Step S34 in FIG. 17 corresponds to step S15 in FIG. 8. Step S35 in FIG. 17 corresponds to step S16 in FIG. 8. Step S47 in FIG. 17 corresponds to step S21 in FIG. 8. Step S48 in FIG. 17 corresponds to step S22 in FIG. 8.

First, in step S31, the CPU 11 obtains the electrocardiogram signal of the driver. Based on the electrocardiogram signal, the CPU 11 calculates the time series data of the distance RRI in step S32. Then, as described above, assuming the exceptional case in FIG. 13, in step S33, the CPU 11 executes a moving average process for processing the time series data of the distance RRI calculated in step S32 so as to detect the low frequency large fluctuation with high accuracy. In this case, in order to remove a frequency component having a frequency higher than the low frequency fluctuation component (i.e., 0.04 Hz to 0.15 Hz), the moving average process is performed. Next, in step S34, the CPU 11 determines whether the vehicle 100 enters into the highway. When the vehicle 100 does not enter into the highway, i.e., when the determination of step S34 is "NO," it repeats steps 31 to S33.

Figure 18:
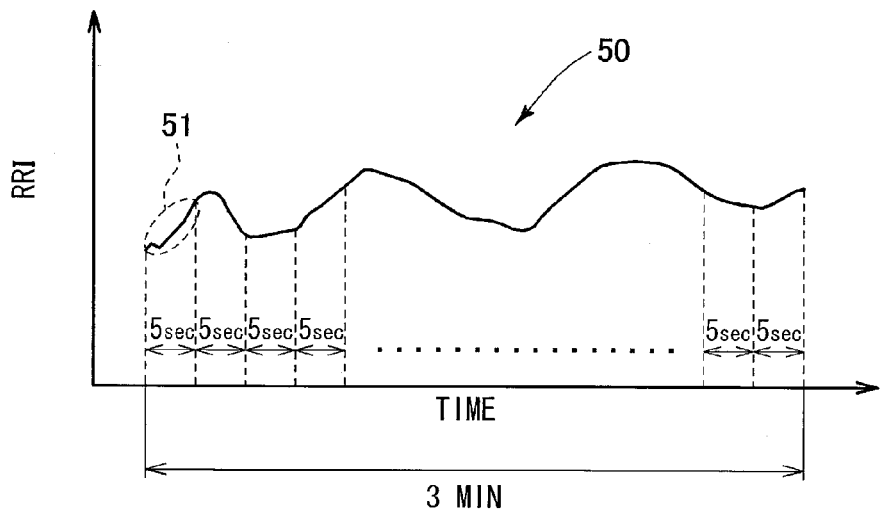
FIG. 18 is a graph showing a standard time series data.
Figure 19:
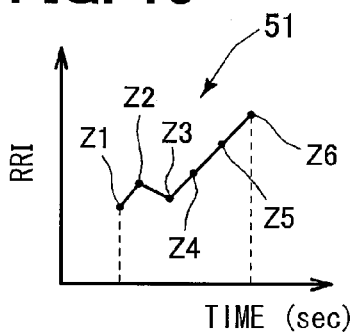
FIG. 19 is a graph showing partial data.

When the vehicle 100 enters into the highway, i.e., when the determination of step S34 is "YES," in step S35, the CPU 11 determines whether the vehicle 100 runs stably in last three minutes, so that the CPU 11 determines the standard time period. When the vehicle 100 runs stably in last three minutes, i.e., when the determination in step S35 is "YES," the CPU 11 determines that the last three minutes provide the standard time period. In steps S36 to S38, the CPU 11 calculates the threshold of the variation of the distance RRI in the low frequency fluctuation component as the detection object according to the time series data of the distance RRI in the standard time period. Here, the threshold of the variation is defined as a variation threshold. Here, FIG. 18 shows the time series data 50 of the distance RRI, which is obtained by processing the time series data in the standard time period in steps S31 to S33. In order to calculate the variation threshold, as shown in FIG. 18, firstly, in step S36, the time series data 50 is divided into multiple partial data items 51 with 5-second width. Here, the five-second width corresponds to the second time width. FIG. 19 shows one of the partial data items 51 obtained in step S36. In the present embodiment, the data time width of the time series data of the distance RRI is set to one second. As shown in FIG. 19, the partial data 51 includes six data points z1 to z6. Here, the data points z1 to z6 are aligned in a time order (chronological order) from z1 to z6. The data point z6 is the present time data.

In step S37, the CPU 11 calculates the five-second addition value Yo of $\Delta$RRI at each partial data item 51. Specifically, in step S37, the CPU 11 calculates the variation $\Delta$RRI of the distance RRI between adjacent two data points among data points z1 to z6. Here, the distance RRI at the data point z is defined as RRI(z). In step S37, the CPU 11 calculates equations of: $\Delta$RRI(1)=RRI(z2)−RRI(z1), $\Delta$RRI(2)=RRI(z3)−RRI(z2), $\Delta$RRI(3)=RRI(z4)−RRI(z3), $\Delta$RRI(4)=RRI(z5)−RRI(z4), and $\Delta$RRI(5)=RRI(z6)−RRI(z5). When the CPU 11 adds the variations of $\Delta$RRI(1) to $\Delta$RRI(5), the five-second addition value Yo of $\Delta$RRI at each partial data item 51 is obtained. Here, the five-second addition value Yo of $\Delta$RRI at each partial data item 51 corresponds to the standard variation (i.e., standard amount of change or standard change amount). Here, in step S37, the CPU 11 calculates each of the standard variations with respect to the partial data items 51.

Figure 20:
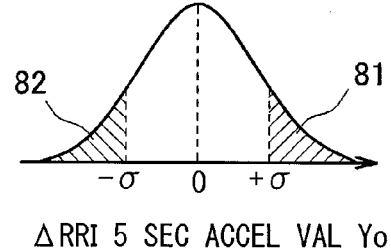
FIG. 20 is a diagram showing a distribution of five-second addition value of ΔRRI in a standard section.

Next, in step S38, the CPU 11 calculates the standard deviation a of the five-second addition values Yo of $\Delta$RRI in the standard time period according to the five-second addition values Yo of $\Delta$RRI obtained in step S37. The standard deviation $\sigma$ is defined as the variation threshold, which is the threshold value of the variation in five seconds of the low frequency large fluctuation. As shown in FIG. 20, the five-second addition value Yo of $\Delta$RRI at each partial data item 51 is distributed with a normal distribution having a center value of zero. Here, the center value corresponds to the average. In step S38, the variation threshold is set to be the large value +$\sigma$ on the positive side from the average (i.e., zero) of the five-second addition value Yo of $\Delta$RRI and the large value −$\sigma$ on the negative side from the average (i.e., zero) of the five-second addition value Yo of $\Delta$RRI.

Figure 21:
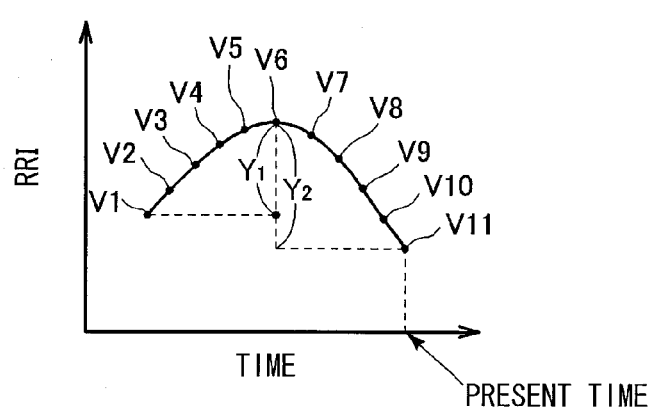
FIG. 21 is a diagram showing time series data in last ten seconds at the present time as standard time.

Under a condition that the CPU 11 calculates the standard deviation a in step S38, the CPU 11 starts to execute the determination for determining whether the driver is in the absentminded state. Specifically, according to the time series data of the distance RRI stored in the memory 12, the CPU 11 retrieves the time series data in last ten seconds at the present time as the standard time. The time series data in last ten seconds corresponds to the first time width data. FIG. 21 shows the time series data 71 retrieved in step S39. As shown in FIG. 21, the time series data 71 includes eleven data points v1 to v11. Here, the data point v11 is the present time data. The data points v1 to v11 are aligned in a time order (chronological order) from v1 to v11.

In step S40, the CPU 11 calculates the variation ΔRRI of the distance RRI between adjacent two data points among data points v1 to v11. Here, the distance RRI at the data point v is defined as RRI(v). In step S40, the CPU 11 calculates equations of: ΔRRI(1)=RRI(v2)−RRI(v1), ΔRRI(2)=RRI(v3)−RRI(v2), ΔRRI(3)=RRI(v4)−RRI(v3), ΔRRI(4)=RRI(v5)−RRI(v4), ΔRRI(5)=RRI(v6)−RRI(v5), ΔRRI(6)=RRI(v7)−RRI(v6), ΔRRI(7)=RRI(v8)−RRI(v7), ΔRRI(8)=RRI(v9)−RRI(v8), ΔRRI(9)=RRI(v10)−RRI(v9), and ΔRRI(10)=RRI(v11)−RRI(v10).

Then, the CPU 11 adds the variations of ΔRRI(1) to ΔRRI(5) obtained from the data points v1-v6 so that the five-second addition value Y1 of ΔRRI is obtained. Here, the data points v1-v6 are disposed in a first half of the ten seconds, which is five seconds. Further, the CPU 11 adds the variations of ΔRRI(6) to ΔRRI(10) obtained from the data points v6-v11 so that the five-second addition value Y2 of ΔRRI is obtained. Here, the data points v6-v11 are disposed in a last half of the ten seconds, which is five seconds. As shown in FIG. 21, the five-second addition value Y1 corresponds to the difference between the distance RRI at the data point v6 and the distance RRI at the data point v1. The five-second addition value Y2 corresponds to the difference between the distance RRI at the data point v11 and the distance RRI at the data point v6.

Then, in step S42, the CPU 11 determines according to the variations ΔRRI calculated in step S40 and the five-second addition values Y1, Y2 calculated in step S41 whether the time series data retrieved in step S39 satisfies a condition of the upper convexity 61 in FIG. 15. Specifically, when the following conditions (a1) to (a4) are satisfied, the CPU 11 determines that the time series data satisfies the condition of the upper convexity 61.

(a1) All of the variations ΔRRI(1) to ΔRRI(5) in the first half of ten seconds are larger than zero.

(a2) The five-second addition value Y1 exceeds the standard deviation +σ of the positive side calculated in step S38.

(a3) All of the variations ΔRRI(6) to ΔRRI(10) in the last half of ten seconds are smaller than zero.

(a4) The five-second addition value Y2 falls below the standard deviation −σ of the negative side calculated in step S38.

The condition (a1) represents that the curve 611 of the distance RRI in the first half of the ten seconds monotonously increases with time. The condition (a2) represents that the five-second addition value Y1 of the curve 611 is disposed in a section 81 in FIG. 20, which is larger than the standard variation +σ of the positive side, so that the five-second addition value Y1 is large on the positive side. The condition (a3) represents that the curve 612 of the distance RRI in the last half of the ten seconds monotonously decreases with time. The condition (a4) represents that the five-second addition value Y2 of the curve 612 is disposed in a section 82 in FIG. 20, which is smaller than the standard variation −σ of the negative side, so that the five-second addition value Y2 is small on the negative side.

When all of the conditions (a1) to (a4) are satisfied, i.e., when the determination of step S42 is "YES," the CPU 11 determines in step S44 that the time series data retrieved in step S39 is the upper convexity 61. In this case, the low frequency large fluctuation is generated.

When at least one of the conditions (a1) to (a4) is not satisfied, i.e., when the determination of step S42 is "NO," it goes to step S43. In step S43, the CPU 11 determines whether the time series data retrieved in step S39 satisfies a condition of the lower convexity 62 in FIG. 16. Specifically, when the following conditions (b1) to (b4) are satisfied, the CPU 11 determines that the time series data satisfies the condition of the lower convexity 62.

(b1) All of the variations ΔRRI(1) to ΔRRI(5) in the first half of ten seconds are smaller than zero.

(b2) The five-second addition value Y1 falls below the standard deviation −σ of the negative side calculated in step S38.

(b3) All of the variations ΔRRI(6) to ΔRRI(10) in the last half of ten seconds are larger than zero.

(b4) The five-second addition value Y2 exceeds the standard deviation +σ of the positive side calculated in step S38.

The condition (b1) represents that the curve 621 of the distance RRI in the first half of the ten seconds monotonously decreases with time. The condition (b2) represents that the five-second addition value Y1 of the curve 621 is disposed in a section 82 in FIG. 20, which is smaller than the standard variation −σ of the negative side, so that the five-second addition value Y1 is small on the negative side. The condition (b3) represents that the curve 622 of the distance RRI in the last half of the ten seconds monotonously increases with time. The condition (b4) represents that the five-second addition value Y2 of the curve 622 is disposed in a section 81 in FIG. 20, which is larger than the standard variation +σ of the positive side, so that the five-second addition value Y2 is larger on the positive side.

When all of the conditions (b1) to (b4) are satisfied, i.e., when the determination of step S43 is "YES," the CPU 11 determines in step S44 that the time series data retrieved in step S39 is the lower convexity 62. In this case, the low frequency large fluctuation is generated. When at least one of the conditions (b1) to (b4) is not satisfied, i.e., when the determination of step S43 is "NO," it goes to step S39 since the time series data retrieved is not the upper convexity 61 and the lower convexity 62. In this case, the CPU 11 retrieves the time series data of the distance RRI in last ten seconds at certain time as the standard time after predetermined time such as one second has elapsed from the process in step S39. Then, the CPU 11 executes steps S40 to S44 so that the CPU 11 determines whether the time series data retrieved is the upper convexity or the lower convexity, i.e., the CPU 11 determines whether the large fluctuation is generated.

In step S44, when the CPU 11 determines that the large fluctuation is generated, i.e., when the CPU 11 determines that the time series data retrieved is the upper convexity or the lower convexity, the CPU 11 controls the memory 12 to store the information showing the time, at which the large fluctuation is generated. Then, based on the information stored in the memory 12 in step S44, the CPU 11 calculates the number W of detection times of the large fluctuation in last three minutes as the determination time period with respect to the present time as the standard time in step S45. Here, the number W of detection times is the number of the large fluctuation included in the determination time period. Here, the number W of the detection times corresponds to the second number. Then, the CPU 11 determines in step S46 whether the number W of the detection times exceeds the threshold Wth, which is stored in the memory 12 preliminary. The threshold Wth corresponds to the second threshold. Here, the threshold Wth may be determined by the experiments such that the number of large fluctuation in last three minutes is experimentally determined when the driver subjectively evaluates that the driver is in the absentminded state. Based on the experimental results of the number of large fluctuation, the threshold Wth is determined. The threshold Wth is, for example, eight times.

When the number W of detection times exceeds the threshold Wth, the CPU 11 determines in step S47 that the driver is in the absentminded state since the low frequency large fluctuation is frequently generated in the time series data of the distance RRI. Then, in step S47, the CPU 11 controls the notification device 25 to notify the driver of the absentminded state. Then, it goes to step S48.

When the number W of detection times is smaller than the threshold Wth, i.e., when the determination of step S46 is "NO," it is considered that the driver is not in the absentminded state, i.e., the driver is in the normal state. In this case, the CPU 11 executes step S48 without executing step S47.

In step S48, the CPU 11 communicates with the navigation device 24, so that the CPU 11 determines whether the vehicle 100 gets off the highway. When the CPU 11 determines that the vehicle 100 does not get off the highway, i.e., when the determination of step S48 is "NO," it returns to step S39. Specifically, when the vehicle runs on the highway, the CPU 11 repeats steps S39 to S48. Thus, the CPU 11 determines at each time whether the driver is in the absentminded state. When the vehicle gets off the highway, i.e., when the determination in step S48 is "YES," the CPU 11 ends to execute the process in FIG. 17. Here, in this case, the CPU 11 starts to execute the process in FIG. 17 again so that it goes to step S31.

Thus, in the present embodiment, in addition to the determination of the absentminded state based on the number of peaks and troughs TP, the CPU 11 executes the determination of the absentminded state based on the number of detection times of the large fluctuation. Thus, even if the CPU 11 does not detect the absentminded state based on one of the above determinations, the CPU 11 detects the absentminded state based on the other of the above determinations. Accordingly, the CPU 11 determines with high accuracy whether the driver is in the absentminded state. Further, even when the CPU 11 detects the characteristics of the large fluctuation such as the peaks and troughs TP and the large fluctuation, the CPU 11 does not use the frequency analysis method such as a Fourier transformation method. Thus, even if the noise is generated, the CPU 11 can determine with high accuracy whether the driver is in the absentminded state. Furthermore, the CPU 11 can determine the absentminded state based on data in the determination time period, i.e., in last three minutes, which is sufficiently short time. Further, since the threshold for determining the absentminded state is set based on the data in the standard time period, which is prepared at the present driving opportunity, a physical condition of the driver at the present driving opportunity and the time zone are reflected on the threshold so that the threshold is appropriately set. Here, the distance RRI may be changed according to the physical condition of the driver. The distance RRI may be changed according to the time zone such as daytime, morning time and night time.

Here, the absentminded state determination apparatus may have different constitution. For example, the absentminded state of the driver may be determined according to the time series data of the cycle of the pulse beat instead of the cycle of the heart rate. Since the pulse beat and the heart rate have similar characteristics, the absentminded state is accurately determined based on the time series data of the cycle of the pulse beat. When the absentminded state is determined based on the time series data of the cycle of the pulse beat, the absentminded state determination apparatus includes a pulse beat sensor for measuring the pulse beat signal instead of the heart rate sensor. Based on the pulse beat signal from the pulse beat sensor, the apparatus obtains the time series data of the cycle of the pulse beat. Further, the standard time period and the determination time period may be different from three minutes. Alternatively, the standard time period and the determination time period may be one minute, five minutes, ten minutes or the like. The standard time period and the determination time period may be set appropriately.

As long as the time period is defined such that the state of the driver is deemed to be normal in the time period, the standard time period may be set to any time period. Specifically, for example, the standard time period may be set to a predetermined time period, which is disposed within a predetermined time range from time when the vehicle enters into the highway other than a certain time period just after the vehicle enters into the highway. For example, the standard time period may be set in three minutes in a range between 4 minutes and 7 minutes elapsed after the vehicle enters into the highway. Thus, the standard time period is not set to the certain time period just after the vehicle enters into the highway, in which the driving condition of the vehicle is not stable. Since the acceleration of the vehicle is large in the certain time, the apparatus prevents from setting the standard time period to the certain time period, which is for example, in a range between zero minute and 4 minutes elapsed after the vehicle enters into the highway. Thus, the standard time period is set to the predetermined time period, in which the vehicle is estimated to stably run on the highway with a constant speed. In this case, the standard time period is in a range between 4 minutes and 7 minutes elapsed after the vehicle enters into the highway. Alternatively, the apparatus may determine the absentminded state when the vehicle runs on main road such as a national road and a prefectural road other than the highway since the number of traffic signs along the main road is small.

The time width of the upper convexity 61 and the lower convexity 62 may be different from ten seconds. The time width of the upper convexity 61 and the lower convexity 62 may be any as long as the time width is longer than the cycle of the high frequency fluctuation, and the low frequency fluctuation can be specified. For example, the time with may be fifteen seconds. In the above embodiment, the large fluctuation is defined in a part, which is not disposed in a range of the five-second addition value Yo of $\Delta$RRI between the large value $-\sigma$ and the large value $+\sigma$ in the standard time period. Alternatively, the large fluctuation may be defined in a part, which is not disposed in a range between $-2\sigma$ and $+2\sigma$ in the standard time period. Alternatively, the large fluctuation may be defined in a part, which is not disposed in a range between $-3\sigma$ and $+3\sigma$ in the standard time period. Thus, the much large fluctuation is detected. Alternatively, the apparatus may execute only one of the determination of the absentminded state based on the number of peaks and troughs TP and the determination of the absentminded state based on the number of detection times of the large fluctuation.

In the above embodiment, the CPU 11 for executing the process in steps S11 and S12 in FIG. 8 and the process in steps S31 and S32 in FIG. 17 corresponds to the obtaining element. The CPU 11 for executing the process in step S13 in FIG. 8 corresponds to the first detection element. The CPU 11 for executing the process in step S19 in FIG. 8 corresponds to the first number counting element. The CPU 11 for executing the process in step S20 in FIG. 8 corresponds to the first determination element. The CPU 11 for executing the process in step S18 in FIG. 8 corresponds to the threshold setting element. The CPU 11 for executing the process in steps S15 and S16 in FIG. 8 and the process in steps S34 and S35 in FIG. 17 corresponds to the time period determination element. The CPU 11 for executing the process in step S16 in FIG. 8 and the process in step S35 FIG. 17 corresponds to the time period judgment element. The CPU 11 for executing the process in step S17 in FIG. 8 corresponds to the standard number counting element. The CPU 11 corresponds to the information obtaining element.

The CPU 11 for executing the process in steps S36 and S37 in FIG. 17 corresponds to the first calculating element. The CPU 11 for executing the process in step S38 in FIG. 17 corresponds to the second calculating element. The CPU 11 for executing the process in steps S39 to S44 in FIG. 17 corresponds to the second detection element. The CPU 11 for executing the process in step S45 in FIG. 17 corresponds to the second counting element. The CPU 11 for executing the process in step S46 in FIG. 17 corresponds to the second determination element. The CPU 11 for executing the process in step S33 in FIG. 17 corresponds to the removing element. The CPU 11 for executing the process in step S42 in FIG. 17 corresponds to the upper convexity determination element. The CPU 11 for executing the process in step S43 in FIG. 17 corresponds to the lower convexity determination element.

The above disclosure has the following aspects.

According to an aspect of the present disclosure, an absentminded state determination apparatus includes: a data obtaining element for obtaining a time series data of a physiological characteristic value of a participant, wherein a fluctuation component is overlapped on the time series data, and the fluctuation component depends on a state of the participant including a normal state and an absentminded state so that the fluctuation component is changeable; a detection element for detecting a plurality of reflecting portions of the time series data, wherein the plurality of reflecting portions reflect on the fluctuation component; a counting element for counting the number of the reflecting portions of the time series data in a determination time period, which is disposed between a determination time and a certain past time; and a determination element for determining according to the number of the reflecting portions at the determination time whether the participant is in the absentminded state. The determination time period has a predetermined time width from the certain past time to the determination time.

The present inventors obtain information such that one of physiological characteristic values has a fluctuation component overlapped on the value, which is changeable according to the state of the participant, i.e., the normal state and the absentminded state. With utilizing the time series data of the physiological characteristic value, the apparatus determines whether the participant is in the absentminded state. The fluctuation component for representing the state of the participant is overlapped on the obtained time series data of the one of physiological characteristic values. Thus, in the time series data includes the reflecting portion, which reflects on the fluctuation component. In the above apparatus, the detection element detects the reflecting portion in the time series data, and the counting element counts the number of the reflecting portions. Thus, the overlapped fluctuation component corresponding to the state of the participant is obtained. Thus, by measuring the number of the reflecting portions, the apparatus can determine whether the participant is in the absentminded state. Even if a noise is overlapped on the time series data, the number of the reflecting portions is not easily affected by the magnitude of the noise. However, in a conventional method for utilizing the Fourier transform method, when the magnitude of the noise is comparatively large, the obtained characteristic value as a spectral power much depends on the frequency component of the noise. Thus, the apparatus can determine the absentminded state without depending on the noise, compared with the conventional method with using a frequency analysis method.

Alternatively, the physiological characteristic value may be a characteristic value of a heart rate or a pulse beat. Further, the detection element may include a first detection element for detecting a peak and a trough as the reflecting portions. The time series data includes a plurality of data points. The peak is a data point having a physiological characteristic value, which is larger than either adjacent data point. The trough is a data point having a physiological characteristic value, which is smaller than either adjacent data point. The counting element includes a first counting element for counting the number of peaks and troughs in the time series data in the determination time period. The number of peaks and troughs provides a first number. The determination element includes a first determination element for determining according to the first number at the determination time whether the participant is in the absentminded state. Furthermore, the absentminded state determination apparatus may further include: a threshold setting element for setting a first threshold for the first number. The first determination element determines that the participant is in the absentminded state when the first number is smaller than the first threshold. Furthermore, the absentminded state determination apparatus may further include: a standard time period determination element for determining a standard time period, which has a same time length as the determination time period, wherein the standard time period is defined in such a manner that the participant is deemed to be in the normal state in the standard time period; and a standard number counting element for counting the number of peaks and troughs in the standard time period, which is defined as a standard number. The threshold setting element sets the first threshold according to the standard number.

Alternatively, the absentminded state determination apparatus may further include: a standard time period determination element for determining a standard time period, which has a same time length as the determination time period, wherein the standard time period is defined in such a manner that the participant is deemed to be in the normal state in the standard time period. The detection element further includes a second detection element for detecting a large fluctuation portion in the time series data as the reflecting portions. The time series data in the standard time period is defined as a standard time series data. The large fluctuation portion is defined in such a manner that a fluctuation component larger than a fluctuation component overlapped on the standard time series data is overlapped on the time series data in the large fluctuation portion. The time series data in the large fluctuation portion is different from the time series data in the standard time period. The counting element further includes a second counting element for counting the number of large fluctuation portions in the time series data in the determination time period. The number of large fluctuation portions provides a second number. The determination element includes a second determination element. The second determination element determines that the participant is in the absentminded state when the second number is larger than a predetermined second threshold. Further, the absentminded state determination apparatus may further include: a first calculation element for dividing the standard time series data with a predetermined time width into a plurality of partial data items, and for calculating a standard change amount of each partial data item, wherein the standard change amount is a variation of the physiological characteristic value in a corresponding partial data item; and a second calculation element for calculating a variation threshold according to the standard change amount. The variation threshold is a threshold of the variation of the physiological characteristic value for detecting the large fluctuation portion, and the second detection element detects the large fluctuation portion having the variation of the physiological characteristic value in the time series data, which is larger than the variation threshold. Furthermore, the absentminded state determination apparatus may further include: a removing element for removing a high frequency fluctuation component from the time series data. A low frequency fluctuation component is overlapped on the time series data when a sympathetic is superior to a parasympathetic. The high frequency fluctuation component has a frequency higher than the low frequency fluctuation component. The first calculation element calculates the standard change amount according to the standard time series data, from which the high frequency fluctuation component is removed, and the second detection element detects the large fluctuation portion in the time series data, from which the high frequency fluctuation component is removed. Further, the second detection element detects an upper convexity or a lower convexity as the large fluctuation portion. The upper convexity is overlapped on the time series data so that the upper convexity protrudes toward a direction, in which the physiological characteristic value increases. The lower convexity is overlapped on the time series data so that the lower convexity protrudes toward a direction, in which the physiological characteristic value decreases. Each of the upper convexity and the lower convexity has a predetermined first time width, which is larger than a cycle of the high frequency fluctuation component, and each of the upper convexity and the lower convexity has the variation of the physiological characteristic value, which is larger than the variation threshold. Further, the first calculation element may divide the standard time series data with a second time width into the plurality of partial data items. The second time width is a half of the first time width, and corresponds to the predetermined time width. The second calculation element calculates the variation threshold according to the standard change amount with respect to the second time width. The second detection element includes an upper convexity determination element and a lower convexity determination element. The time series data in the determination time period is divided with the first time width into a plurality of first time width partial data items. Each first time width partial data item includes a first half item and a last half item, each of which has the second time width. The physiological characteristic value in the first half item is defined as a first half physiological characteristic value, and the physiological characteristic value in the last half item is defined as a last half physiological characteristic value. The upper convexity determination element determines that the first time width partial data item provides the upper convexity when the first half physiological characteristic value monotonically increases with time, the last half physiological characteristic value monotonically decreases with time, and each of the variation of the first half physiological characteristic value and the variation of the last half physiological characteristic value is larger than the variation threshold, and the lower convexity determination element determines that the first time width partial data item provides the lower convexity when the first half physiological characteristic value monotonically decreases with time the last half physiological characteristic value monotonically increases with time, and each of the variation of the first half physiological characteristic value and the variation of the last half physiological characteristic value is larger than the variation threshold. Further, the second calculation element may calculate the variation threshold, which is a standard deviation of the standard change amount. Further, the participant may be a driver of a vehicle. The absentminded state determination apparatus may further include: an information obtaining element for obtaining at least one of vehicle acceleration information and vehicle speed information. The standard time period determination element includes a standard time period judgment element for judging a time period, in which the vehicle runs stably, according to the at least one of vehicle acceleration information and vehicle speed information, and the standard time period determination element selects one of time periods, which are judged as stable running periods by the standard time period judgment element, as the standard time period.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. An absentminded state determination apparatus comprising:
    a data obtaining element for obtaining time series data, wherein at least portions of data points in the time series data are time intervals between adjacent pulse beats or heart beats of a participant;
    a detection element for detecting a plurality of peaks and troughs of the time series data;
    a counting element for counting the number of the peaks and troughs detected by the detection element in a determination time period; and
    a determination element for determining, without using a Fourier transform, according to the number of the peaks and troughs counted by the counting element whether the participant is in an absentminded state,
    wherein each peak is a data point, which is larger than each adjacent data point,
    wherein each trough is a data point, which is smaller than each adjacent data point,
    wherein each peak represents the largest time interval in a region of the time series data,
    wherein each trough represents the smallest time interval in a region of the time series data.

2. The absentminded state determination apparatus according to claim 1, further comprising:
    a threshold setting element for setting a threshold for the number of the peaks and troughs,
    wherein the determination element determines that the participant is in the absentminded state when the number of peaks and troughs is smaller than the threshold.

3. The absentminded state determination apparatus according to claim 2, further comprising:
    a standard time period determination element for determining a standard time period, which has a same time length as the determination time period, wherein the standard time period is defined in such a manner that the participant is deemed to be in a normal state in the standard time period; and
    a standard number counting element for counting the number of peaks and troughs in the standard time period, which is defined as a standard number, wherein the threshold setting element sets the threshold according to the standard number.

4. The absentminded state determination apparatus according to claim 3,
wherein the participant is a driver of a vehicle,
the absentminded state determination apparatus further comprising:
an information obtaining element for obtaining at least one of vehicle acceleration information and vehicle speed information,
wherein the standard time period determination element includes a standard time period judgment element for judging a time period, in which the vehicle runs stably, according to the at least one of vehicle acceleration information and vehicle speed information, and
wherein the standard time period determination element selects one of time periods, which are judged as stable running periods by the standard time period judgment element, as the standard time period.

5. The absentminded state determination apparatus of claim 1,
the peaks and troughs of the time series data, in which the counting element counts the number of peaks and troughs, include noise of the time series data obtained by the data obtaining element without removal by the Fourier transform, and
the determining by the determination element as to whether the participant is in the absentminded state uses the peaks and troughs counted by the counting element in the time series data which include the noise as obtained by the data obtaining element without removal by the Fourier transform.

6. An absentminded state determination apparatus comprising:
a data obtaining element for obtaining time series data, wherein at least portions of data points in the time series data are time intervals between adjacent pulse beats or heart beats of a participant;
a detection element for detecting a plurality of peaks and troughs of the time series data;
a counting element for counting the number of the peaks and troughs detected by the detection element in a determination time period; and
a determination element for determining, without using a Fourier transform, according to the number of the peaks and troughs counted by the counting element whether the participant is in an absentminded state,
wherein a standard time period is defined, without using a Fourier transform, in such a manner that the participant is deemed to be in a normal state in the standard time period,
wherein the standard time period has a same time length as the determination time period,
wherein the time series data in the standard time period is defined as standard time series data,
wherein each peak is a data point, which is larger than each adjacent data point and larger than corresponding standard time series data,
wherein each trough is a data point, which is smaller than each adjacent data point and smaller than corresponding standard time series data,
wherein each peak represents the largest time interval in a region of the time series data,
wherein each trough represents the smallest time interval in a region of the time series data.

7. The absentminded state determination apparatus according to claim 6, further comprising:

a first calculation element for dividing the standard time series data with a predetermined time width into a plurality of partial data items, and for calculating a standard change amount of each partial data item, wherein the standard change amount is a variation of the heart rate or the pulse beat of the participant in a corresponding partial data item;
a second calculation element for calculating a variation threshold according to the standard change amount;
a second detection element for detecting a large fluctuation portion in the time series data as the peaks and troughs, wherein the large fluctuation portion is defined in such a manner that a fluctuation component larger than a fluctuation component overlapped on the standard time series data is overlapped on the time series data in the large fluctuation portion, and wherein the time series data in the large fluctuation portion is different from the time series data in the standard time period;
a second counting element for counting the number of large fluctuation portions in the time series data in the determination time period;
a second determination element determines that the participant is in the absentminded state when the number of large fluctuation portions is larger than a predetermined second threshold,
wherein the variation threshold is a threshold of the variation of the heart rate or the pulse beat of the participant for detecting the large fluctuation portion, and
wherein the second detection element detects the large fluctuation portion having the variation of the heart rate or the pulse beat of the participant in the time series data, which is larger than the variation threshold.

8. The absentminded state determination apparatus according to claim 7, further comprising:
a removing element for removing a high frequency fluctuation component from the time series data,
wherein a low frequency fluctuation component is overlapped on the time series data when a sympathetic is superior to a parasympathetic,
wherein the high frequency fluctuation component has a frequency higher than the low frequency fluctuation component,
wherein the first calculation element calculates the standard change amount according to the standard time series data, from which the high frequency fluctuation component is removed, and
wherein the second detection element detects the large fluctuation portion in the time series data, from which the high frequency fluctuation component is removed.

9. The absentminded state determination apparatus according to claim 8,
wherein the second detection element detects an upper convexity or a lower convexity as the large fluctuation portion,
wherein the upper convexity is overlapped on the time series data so that the upper convexity protrudes toward a direction, in which the heart rate or the pulse beat of the participant increases,
wherein the lower convexity is overlapped on the time series data so that the lower convexity protrudes toward a direction, in which the heart rate or the pulse beat of the participant decreases,
wherein each of the upper convexity and the lower convexity has a predetermined first time width, which is larger than a cycle of the high frequency fluctuation component, and wherein each of the upper convexity and the lower convexity has the variation of the heart rate or the pulse beat of the participant, which is larger than the variation threshold.

10. The absentminded state determination apparatus according to claim 9,
   wherein the first calculation element divides the standard time series data with a second time width into the plurality of partial data items,
   wherein the second time width is a half of the first time width, and corresponds to the predetermined time width,
   wherein the second calculation element calculates the variation threshold according to the standard change amount with respect to the second time width,
   wherein the second detection element includes an upper convexity determination element and a lower convexity determination element,
   wherein the time series data in the determination time period is divided with the first time width into a plurality of first time width partial data items,
   wherein each first time width partial data item includes a first half item and a last half item, each of which has the second time width,
   wherein the heart rate or the pulse beat of the participant in the first half item is defined as a first half physiological characteristic value, and the heart rate or the pulse beat of the participant in the last half item is defined as a last half physiological characteristic value,
   wherein the upper convexity determination element determines that the first time width partial data item provides the upper convexity when the first half physiological characteristic value monotonically increases with time, the last half physiological characteristic value monotonically decreases with time, and each of the variation of the first half physiological characteristic value and the variation of the last half physiological characteristic value is larger than the variation threshold, and
   wherein the lower convexity determination element determines that the first time width partial data item provides the lower convexity when the first half physiological characteristic value monotonically decreases with time, the last half physiological characteristic value monotonically increases with time, and each of the variation of the first half physiological characteristic value and the variation of the last half physiological characteristic value is larger than the variation threshold.

11. The absentminded state determination apparatus according to claim 10,
   wherein the second calculation element calculates the variation threshold, which is a standard deviation of the standard change amount.

12. The absentminded state determination apparatus of claim 6,
   the peaks and troughs of the time series data, in which the counting element counts the number of peaks and troughs, include noise of the time series data as obtained by the data obtaining element without removal by the Fourier transform, and
   the determining by the determination element as to whether the participant is in the absentminded state uses the peaks and troughs counted by the counting element in the time series data which include the noise obtained by the data obtaining element without removal by the Fourier transform.

* * * * *